United States Patent [19]
Tückmantel et al.

[11] Patent Number: 6,156,912
[45] Date of Patent: Dec. 5, 2000

US006156912A

[54] 8↔8, 6↔6, AND 6↔8 CATECHIN AND EPICATECHIN DIMERS AND METHODS FOR THEIR PREPARATION

[75] Inventors: Werner Tückmantel, Washington, D.C.; Alan P. Kozikowski, Princeton; Leo J. Romanczyk, Jr., Hackettstown, both of N.J.

[73] Assignee: Mars, Incorporated, McLean, Va.

[21] Appl. No.: 09/289,565

[22] Filed: Apr. 9, 1999

[51] Int. Cl.$^7$ ............................................. C07D 311/62
[52] U.S. Cl. ......................................................... 549/399
[58] Field of Search ............................................. 549/399

[56] References Cited

U.S. PATENT DOCUMENTS

| | | | |
|---|---|---|---|
| 5,554,645 | 9/1996 | Romanczyk, Jr. et al. | 514/453 |
| 5,912,363 | 6/1999 | Nafisi-Movaghar et al. | 549/399 |

FOREIGN PATENT DOCUMENTS

| | | |
|---|---|---|
| 0039844 | 11/1978 | European Pat. Off. . |
| 0096 007 | 5/1983 | European Pat. Off. . |
| 0216 936 | 4/1987 | European Pat. Off. . |
| 15 18 003 | 1/1969 | Germany . |
| 58-154571 | 9/1983 | Japan . |
| 62-48677 | 3/1987 | Japan . |
| 41 90774 | 11/1990 | Japan . |
| WO 90/13304 | 11/1990 | WIPO . |
| WO 97/36597A | 10/1997 | WIPO . |

OTHER PUBLICATIONS

Balde, A.M. et al., Phytochemistry, vol. 30, No. 12. p. 4129–4135 (1991).
Lee, M.J. et al., *Agricultural Chemistry and Biotechnology*, 41(1): p. 110–117 (1998).
Kiatgrajai P., et al J. Org. Chem. 47, 2910–2012 (1982).
Porter, L.J. "Flavans and Proanthocyanidins" from *"The Flavonoids"* Ed. J.B. Harborne, Chapmen and Hall Ltd., p 21–62 (1988).
Nonaka G–I., *Chem. Pharm. Bull.* 31 (11) 3906–3914 (1983).
Nonaka G–I., et al *J. Chem Soc. Perkin Trans.*, I: p. 2139–2145 (1983).
Roux, D.G. et al., *Progress in the Chemistry of Organic Natural Products* 41. p. 47–76, (1982).
Botha, J.J. et al, *J. Chem. Soc. Perkin I*, 527–533 (1982).
Botha, J.J. et al, *J. Chem. Soc. Perkin I*, 1235–1245 (1980).
Boukharta, M. et al, Presented at the XVIth International Conference of the Groupe Polyphenols, Lisbon, Portugal, Jul. 13–16, 1992.
Roux, D.G. et al, *J. Agric. Food Chem.* 28:216–222 (1980).
Czochanska, Z., et al., *J. Chem. Soc. Perkin I*:2278–2286 (1979).
Chu, S.C. et al, *J. of Natural Products*, 55, (2), 179–183 (1992).
Delcour, J.A. et al., *J. Chem. Soc. Perkin Trans I* 1711–1717 (1983).
Deschner, E.E. et al, Carcinogenesis, 7, 1193–1196, (1991).
Ferriera, D. et al, *Tetrahedron*, 48, (10), 1743–1803 (1992).

Foo, L.Y. & Hemingway, R.W., *J. Chem. Soc., Perkin I*, 1235–1245 (1981).
Foo, L.Y. et al, *J. Chem. Soc, Chem. Commun.*, 85–86 (Sep. 1984).
Foo, L.Y. et al, *J. Chem. Soc. Perkin I* 1983:1535–1543.
Funayama, M. et al, *Biosci. Biotech. Biochem.*, 58, (5), 817–821 (1994).
Ho, C.T., Lee C.Y., and Huang, M.T. Eds., Phenolic Compounds in Foods and Their Effects on Health I. Analysis, Occurrence and Chemistry, ACS Symposium Series 506, American Chemical Society, Washington D.C. (1992).
Huang, M.T., Ho, C.T. and Lee C.Y., Eds. Phenolic Compounds in Foods and Their Effects on Health II. Antioxidants and Cancer Prevention, ACS Symposium Series 507, American Chemical Society, Washington D.C. (1992).
Hundt, H.K. et al, *J. Chem. Soc. Perkin I:* 1227–1234 (1981).
Kahne, D., et al, *J. Am. Chem. Soc.*, 116881 (1989).
Kashiwada, Y., et al., *Chem. Pharm. Bull.* 34:4083–4091 (1986).
Kato, R. et al, Carcinogenesis, 1301–1305 (1983).
Kawamoto, H, et al *Synthetic Communications*, 26(3), 531–534 (1996).
Kawamoto, H. et al, *Mokazai gakkaishi*, 37, (5) 488–493 (1991).
Keogh et al, *Chem. Ind.* (London) 2100–1 (1961). Abstract only.
Khanbabaee, K. et al, *Tetrahedron*, 53:31, 10725–10732 (1997).
Kitao et al, *Biosci. Biotech. Biochem.* 59(11), 2167–2169, (1995).
Kolodziej, H., *Phytotherapy Research*, 9:410–415 (1995).
Newman, R.H., *Magnetic Resonance in Chemistry* 25:118–124 (1987).
Okuda, T. et al, Molecular Structures and Pharmacological activities of Polyphenols—Oligomeric Hydrolyzable Tannins and Others—Presented at the XVIth International Conference of the Groupe Polyphenols, Lisbon, Portugal, Jul. 13–16, 1992.
Pierre. M.C. et al. *Tetrahedron Letters* 38, (32), 5639–5642 (1997).
Roux & Ferreira, *Fortschritte d. Chemie Org. Naturst.*, pp. 47–76 (1982).
Steenkamp et al, *Tetrahedron Letters*, 26, (25), 3045–3048 (1985).
Steynberg, P.J. et al, *Tetrahedron* 54:8153–8158 (1998).
Toshima, K., Tatsuta, K., *Chem. Rev.*, 1503–1531 (1993).
Van Rensberg et al, *J. Chem. Soc. Chem. Commun.* 24:2705–2706.
Weinges, K. et al. *Chem. Ber.* 103, 2344–2349 (1970).

*Primary Examiner*—Bernard Dentz
*Attorney, Agent, or Firm*—Clifford Chance Rogers Wells LLP

[57] ABSTRACT

Novel catechin and epicatechin dimers with (8↔8), (6↔6), and (8↔6) linkages are prepared, as well as digallated dimers. A novel process for preparing these compounds is disclosed which involves the oxidative or reductive coupling of protected monomers.

17 Claims, No Drawings

8↔8, 6↔6, AND 6↔8 CATECHIN AND EPICATECHIN DIMERS AND METHODS FOR THEIR PREPARATION

FIELD OF THE INVENTION

This invention relates to synthetic catechin and epicatechin dimers, derivatives thereof, and methods for making and using them.

RELATED BACKGROUND ART

Polyphenols are a highly diverse group of compounds (Ferreira, D., Steynberg, J. P., Roux, D. G. and Brandt, E. V., *Tetrahedron*, 48, (10), 1743–1803 (1992)) which widely occur in a variety of plants, some of which enter into the food chain. In many cases, they represent an important class of compounds present in the human diet. Although some of the polyphenols are considered to be non-nutritive, interest in these compounds has arisen because of their possible beneficial effects on health.

For instance, quercetin (a flavonoid) has been shown to possess anticarcinogenic activity in experimental animal studies (Deschner, E. E., Ruperto, J., Wong, G. and Newmark, H. L., *Carcinogenesis*, 7, 1193–1196 (1991) and Kato, R., Nakadate, T., Yamamoto, S. and Sugimura, T., *Carcinogenesis*, 4, 1301–1305 (1983)). (+) - Catechin and (−) - epicatechin (flavan-3-ols) have been shown to inhibit Leukemia virus reverse transcriptase activity (Chu S. C., Hsieh, Y. S. and Lim, J. Y, *J. Nat. Prod.*, 55, (2), 179–183 (1992)). Nobotanin (an oligomeric hydrolyzable tannin) has also been shown to possess anti-tumor activity (Okuda T., Yoshida, T., and Hatano, T., Molecular Structures and Pharmacological Activities of Polyphenols—Oligomeric Hydrolyzable Tannins and Others—Presented at the XVIth International Conference of Groupe Polyphenols, Lisbon, Portugal, July 13–16, 1992). Statistical reports have also shown that stomach cancer mortality is significantly lower in the tea producing districts of Japan. Epigallocatechin gallate has been reported to be the pharmacologically active material in green tea that inhibits mouse skin tumors (Okuda et al., ibid.). Ellagic acid has also been shown to possess anticarcinogenic activity in various animal tumor models (Boukharta M., Jalbert, G. and Castonguay, A., Efficacy of Ellagitannins and Ellagic Acid as Cancer Chemopreventive Agents —Presented at the XVIth International Conference of the Groupe Polyphenols, Lisbon, Portugal, July 13–16, 1992). Proanthocyanidin oligomers have been disclosed (JP 4-190774) by the Kikkoman Corporation for use as antimutagens. The use of phenolic compounds in foods and their modulation of tumor development in experimental animal models has been recently presented at the 202nd National Meeting of The American Chemical Society (Phenolic Compounds in Foods and Their Effects on Health I, Analysis, Occurrence & Chemistry, Ho, C. T., Lee, C. Y., and Huang, M. T. editors, ACS Symposium Series 506, American Chemical Society, Washington D.C. (1992); Phenolic Compounds in Foods and Their Effects on Health II. Antioxidants & Cancer Prevention, Huang, M. T., Ho, C. T., and Lee, C. Y. editors, ACS Symposium Series 507, American Chemical Society, Washington, D.C. (1992)). Procyanidins, and particularly higher procyanidin oligomers, have recently been found to possess a broad spectrum of biological activity.

To determine structure-activity relationships among many possible regio and stereo-isomers comprising any given oligomer, synthesis methods have been developed. These methods focus on the typical (4→6), (4→8), (6→4), and (8→4) linkages comprising linear and branded procyanidin oligomers. In addition to these linkages, the stereochemistry of the linkages at the C-4 position are dependent upon the monomer comprising these linkage positions.

For instance, when (+)-catechin, designated herein as C, is linked to another C or to (−)-epicatechin, designated herein as EC, the linkages are advantageously (4→6) or (4→8). When EC is linked to C another EC, the linkages are advantageously (4β→6) or (4β→8). For linkages to a branched oligomer the stereochemical linkages are (6→4α), (6→4β), (8→4α), (8→4β).

However, other linkage positions are possible among monomers comprising an oligomer. These are the (8↔8), (6↔6), and (6↔8) linkages with representative structures shown below. Since oligomers comprised of these unusual linkages are either rare or unknown in nature, similar or new uses for these compounds and their derivatives can be obtained through biological assessment.

Hence, there is interest in synthesizing these oligomers comprising these linkages.

SUMMARY OF THE INVENTION

This invention is directed to novel 8↔8, 6↔6, 8↔6 catechin and epicatechin dimers and gallated dimers and to processes for their preparation. The compounds prepared by the processes of this invention may be purified, for example, by HPLC. The compounds of this invention may be used as anti-cancer agents.

(8↔8), (6↔6), (8↔6) Catechin and/or epicatechin dimers having the following structures:

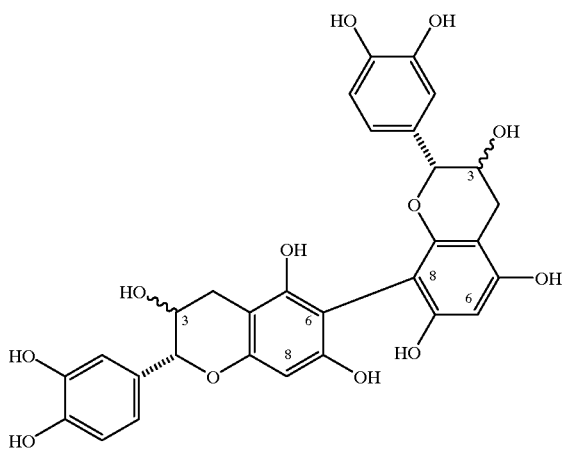

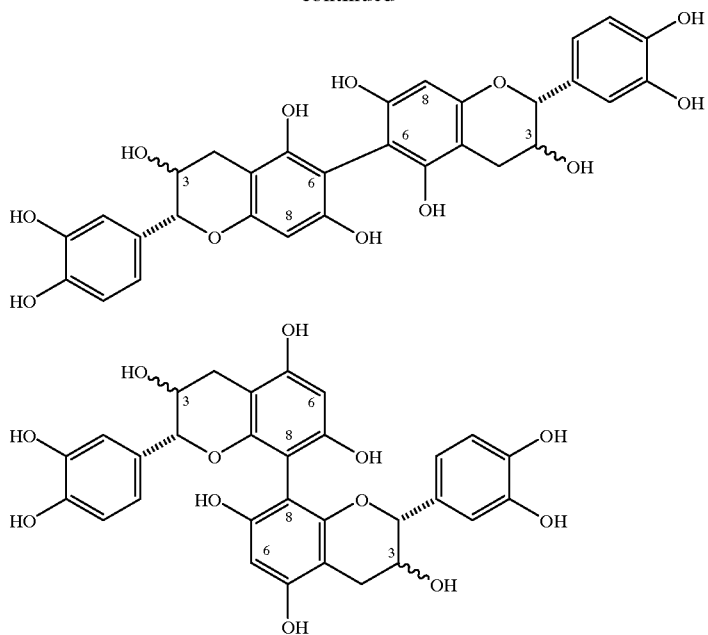
(8↔8), (6↔6), (8↔6) Catechin and/or epicatechin digallate dimers having the following structures:
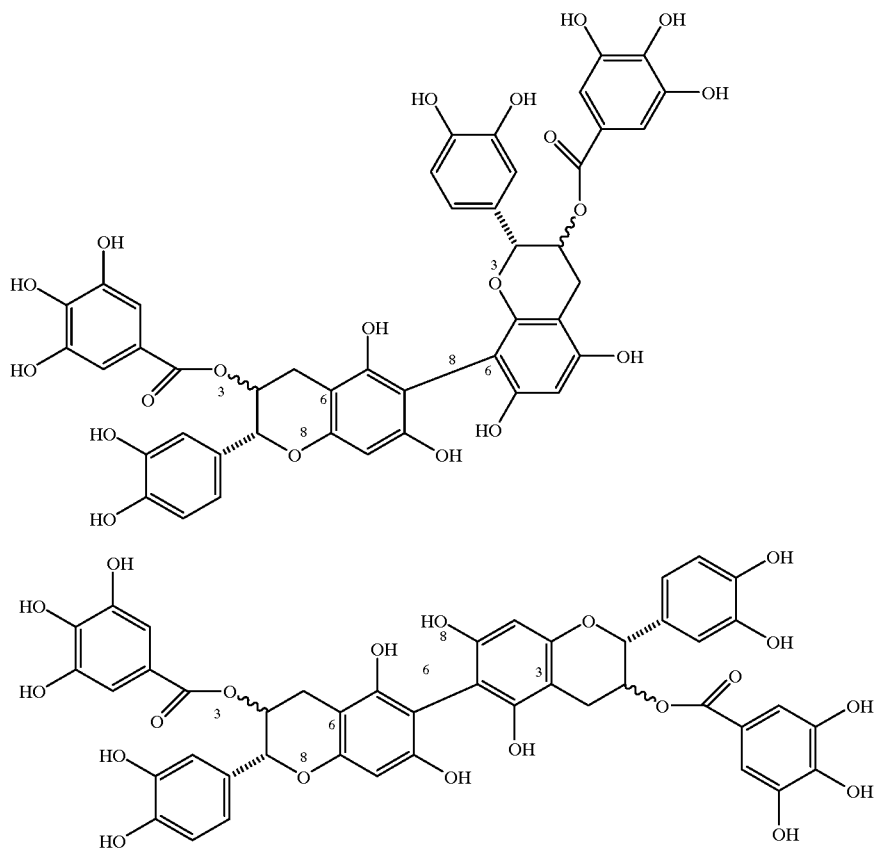

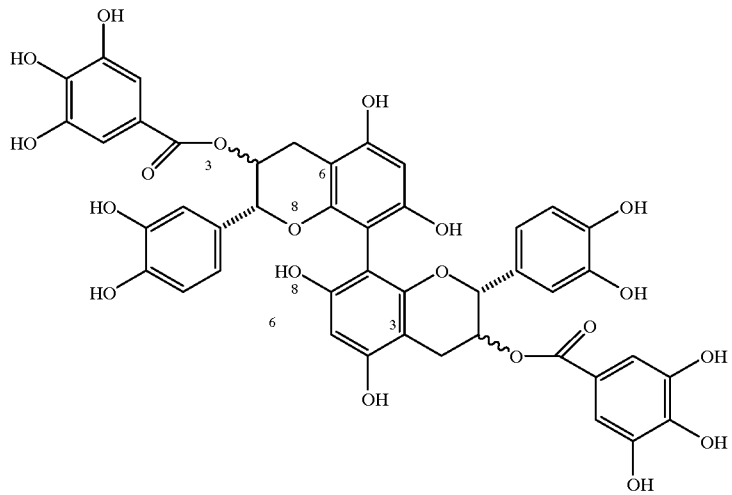

The (8↔8) dimers were prepared by a process which comprises the steps of: (a) protecting the phenolic hydroxyl groups of an epicatechin and/or catechin monomers with a first protecting group; (b) protecting the 3-hydroxyl groups of the monomers with a second protecting group; (c) halogenating the C-8 position e.g., with N-bromosuccinimide, to produce an 8-bromo compounds; (d) reacting the 8-bromo compounds with alkyl lithium e.g., tert-butyllithium or butyllithium to produce alkyl lithium compounds; (e) performing an oxidative or reductive coupling of the alkyl lithium compounds by performing a halogen metal exchange wherein the alkyl lithium is added to form an 8-lithium compound followed by the addition of ferric chloride to effect the (8↔8) coupling; and (f) deprotecting the (8↔8) compounds.

An alternate process comprises carrying out the above steps (a) through (c), and then performing a reductive coupling of the halogenated compounds, e.g., by using a zero valence nickel reagent in conjunction with the corresponding metal powder followed by deprotection.

When benzyl groups are used for protection of the phenolic hydroxy groups or the 3-hydroxyl groups, the deprotection is carried out by hydrogenolysis. When tetrahydropyranyl is used for the protection the 3-hydroxdyl groups the tetrahydropyranyl protecting groups are removed first and then benzyl protecting groups are removed.

A process for preparing the (6↔6) Catechin and/or epicatechin dimer digallate comprises the steps of:

(a) protecting the phenolic hydroxyl groups of the epicatechin or catechin monomers with a first protecting group;
(b) halogenating the C-6 and the C-8 positions;
(c) protecting the 3-hydroxyl groups with a second protecting group, e.g., using tert-butyldimethylsilyl;
(d) selectively removing the 8-halo groups; e.g., bromo groups;
(e) performing an oxidatively or reductively coupling of the 6-halo compounds;
(f) deprotecting the 3-hydroxyl groups;
(g) esterifying the 3-positions with tri-O-benzylgalloylchloride; and
(h) at the C-3 position; and
(g) deprotecting the phenolic hydroxyl groups to form the (6↔6) free dimer digallate.

The (6↔8) dimers are prepared from catechin and/or epicatechin by a process which comprises the steps of: (a) performing an oxidative coupling of a mixture of 6-bromo and 8-bromo catechin and/or epicatechin monomers to produce a mixture of (8↔8), (6↔8), and (8↔8) dimers; and (b) separating the mixture HPLC. Alternatively, the (6↔8) dimers are prepared by a process which comprises the steps of: (a) forming an aryl boronic acid from either the 6-bromo or 8-bromo catechin and/or epicatechin monomers using a halogen metal exchange reaction quenched by trimethyl borate followed by an aqueous-acidic workup to produce the free acid; and (b) exposing the mixture to a palladium catalyst to effect coupling.

DETAILED DESCRIPTION OF THE INVENTION

Suitable protecting groups for the phenolic hydroxyl groups of the monomers for use herein include those protecting groups that may be introduced into the monomers and removed without racemization or degradation of the monomers and that are stable to the conditions used for the oxidative or reductive coupling reaction. Methods for protecting and deprotecting hydroxyl groups are well known to those skilled in the art and are described in "Protective Groups in Organic Synthesis," T. W. Greene, John Wiley & Sons. Preferably, the protecting groups are benzyl groups, all of which are readily removed in one step.

Suitable protecting groups for the 3-hydroxyl groups include benzyl, tetrahydropyranyl, and the like. References disclosing the use of ferric chloride ($FeCl_3$) in the oxidative coupling of 2 aryl to aryl 2: C. A. Broka, Tetrahedron Lett. 32, 859 (1991).

References disclosing reductive coupling of 2 aryl to aryl 2 by means of zerovalent nickel reagents (in most cases, zerovalent nickel is generated in situ from Ni(II) salts/complexes and a reducing agent) include the following:

R. H. Mitchell et al., J. Am. Chem. Soc. 106, 7776 (1984); H. Matsumoto et al., J. Org. Chem. 48, 840 (1983); S. Inaba et al., Tetrahedron Lett. 23, 4215 (1982); S. Knapp et al., J. Org. Chem. 58, 997 (1993); K. Takagi et al., Bull. Chem. Soc. Jpn. 57, 1887 (1984); M. Iyoda et al., Bull. Chem. Soc. Jpn. 63, 80 (1990) (the most important reference) K. Takagi et al., Chem. Lett., 917 (1979); M. A. Fox et al., J. Org. Chem. 56, 3246 (1991); Y. Rollin et al., J. Organomet.

Chem. 303, 131 (1986);R. Vanderesse et al., J. Organomet. Chem. 264, 263 (1984); B. Loubinoux et al., Tetrahedron Lett., 3951 (1977);

Reference disclosing Suzuki coupling for the synthesis of unsymmetrical biaryls (aryl Br+aryl'B (OH)2 to ArAr' in the presence of a Paladium (Pd) compound as the catalyst include the following:

R. B. Miller and S. Dugar, Organometallics 3, 1261 (1984); M. A. F. Brandao et al., Tetrahedron Lett. 34, 2437 (1993); M. Sato et al., Chem. Lett., 1405 (1989); S. P. Maddaford and B. A. Keay, J. Org. Chem. 59, 6501–3 (1994) (a key reference); M. J. Burk et al., J. Am. Chem. Soc. 116, 10847–8 (1994); S. W. Wright et al., J. Org. Chem. 59, 6095–7 (1994) (a key reference); G. B. Smith et al., J. Org. Chem. 59, 8151–6 (1994); T. I. Wallow and B. M. Novak, J. Org. Chem. 59, 5034–7 (1994) (a key reference); X. Yue et al., Tetrahedron Lett. 37, 8213–6 (1996); J. W. Benbow and B. L. Martinez, Tetrahedron Lett. 37, 8829–32 (1996); M. Beller et al., Angew. Chem. 107, 1992–3 (1995), (sometimes boronate esters rather than the free boronic acids are used).

Stereoisomers of the dimers are encompassed within the scope of the invention. The stereochemistry of the substituents on a polyphenol monomeric unit of the dimer may be described in terms of their relative stereochemistry, "alpha/beta" or "cis/trans", or in terms of absolute stereochemistry, "R/S". The term "alpha" ($\alpha$) indicates that the substituent is oriented below the plane of the flavan ring, whereas, "beta" ($\beta$) indicates that the substituent is oriented above the plane of the ring. The term "cis" indicates that two substituents are oriented on the same face of the ring, whereas "trans" indicates that two substituents are oriented on opposite faces of the ring. The terms R and S are used to denote the arrangement of the substituents about a center of chirality, based on the ranking of the groups directly attached to that center. The interflavan bond between the substituted aromatic rings constitutes a chiral axis from which two atropisomers could arise.

EXAMPLE 1

Preparation of (2R,3S, trans)-5,7,3',4'-Tetra-O-benzylcatechin

A solution of (+)-catechin (65.8 g, 226.7 mmol, anhydrous), dissolved in anhydrous dimethylformamide (DMF, 720 mL), was added dropwise, at room temperature over a period of 80 min, to a stirred suspenson of sodium hydride, 60% in oil, (39 g, 975 mmol, 4.3 eq.) in DMF (180 mL). (S. Miura et al., *Radioisotopes*, 32, 225–230 1993). After stirring for 50 min, the flask was placed in a –10° C. NaCl/ice bath. Benzyl bromide (121 mL, 1.02 mol, 4.5 eq.) was added dropwise within 80 min. and the brown reaction mixture warmed to room temperature, with stirring, overnight. The resulting reaction mixture was evaporated and the resulting candy-like solid was dissolved, with heating and stirring, in two portions of solvent, each consisting of 200 mL of chloroform (CHCl$_3$) and 100 mL of water. The phases were separated, and the aqueous phase extracted with chloroform (20 mL), and the combined organic phases washed with water (100 mL), dried over Magnesium sulphate (MgSO$_4$) and evaporated. The residue was purified by chromatography on silica gel (42×10 cm; ethyl acetate/chloroform/hexane 1:12:7) to provide, after evaporation and drying in vacuo, 85 g of crude product, which was recrystallized from trichloroethylene (1.3 L) to provide 35.1 g (24%) of an off-white powder. $^1$H NMR (CDCl$_3$) $\delta$ 7.47–7.25 (m, 20 H), 7.03 (s, 1 H), 6.95 (s, 2 H), 6.27, 6.21 (ABq, 2 h, J=2 Hz), 5.18 (s, 2 H), 5.17 (narrow ABq, 2 H), 5.03 (s, 2 H), 4.99 (s, 2 H), 4.63 (d, 1 H, J=8.5 Hz), 4.00 (m, 1 H), 3.11, 2.65 (ABq, 2 H, J=16.5 Hz, both parts d with J=5.5 and 9 Hz, resp.), 1.59 (d, 1 H, J=3.5 Hz); IR (film) 3440 (br), 1618, 1593, 1513, 1499, 1144, 1116, 733, 696 cm$^{-1}$; MS m/z 650 (M+, 0.5%), 319, 181, 91.

Alternatively, the tetra-O-benzyl (+)-catechin may be prepared using the method described by H. Kawamoto et al, *Mokazai Gakkaishi*, 37, (5) 488–493 (1991), using Potassium carbonate and Benzyl bromide in DMF. Partial racemization of catechin, at both the 2- and 3-positions, was observed by M.-C. Pierre et al., *Tetrahedron Letters*, 38, (32) 5639–5642 (1997).

EXAMPLE 2

Preparation of (2R)-5,7,3',4' Tetrakis (benzyloxy) flavan-3-one

Freshly prepared Dess-Martin periodinane (39.0 g, 92 mmol, prepared by the method of D. B. Dess and J. C. Martin, *J. Am. Chem. Soc.* 113, 7277–7287 (1991) and R. E. Ireland and L. Liu, *J. Org. Chem.* 58, 2899 (1993)), was added at room temperature, all at once, to a stirred solution of the tetra-O-benzyl catechin according to the preceding example (54.4 g, 83.8 mmol) in Methylene chloride (420 mL). Within 1.5 hours, approximately 30 mL of water-saturated Methylene chloride was added dropwise to the reaction mixture to form a turbid amber-coloured solution. (S. D. Meyer and S. L. Schreiber, *J. Org. Chem.*, 59, 7549–7552 (1994)). Twenty minutes thereafter, the reaction mixture was diluted with a saturated solution of Sodium carbonate (NaHCO$_3$, 500 mL) and a 10% aqueous solution of Na$_2$S$_2$O3.5H$_2$O (200 mL). The phases were separated and the aqueous phase extracted with 50 mL of Methylene chloride. The combined organic phases were filtered over silica gel (24×9 cm, chloroform/etyl acetate/9:1). The eluate was evaporated and dried in vacuo to obtain 50.1 g (92%) of the ketone, which was purified by recrystallization from chloroform/ether: mp 144–144.5° C.; [$\alpha$]$_D$+38.5°, [$\alpha$]$_{546}$+ 48.7° (chloroform, c 20.8 g/L); 1 H NMR (CDCl$_3$) $\delta$ 7.45–7.26 (m, 20 H), 6.96 (s, 1 H), 6.88, 6.86 (ABq 2 H, J=8 Hz, B part d with J=1.5 Hz), 6.35 (narrow ABq, 2 H), 5.24 (s, 1 H), 5.14 (s, 2 H), 5.10 (narrow ABq, 2 H), 5.02 (s, 2 H), 5.01 (s, 2 H), 3.61, 3.45 (ABq, 2 H, J=21.5 Hz).

EXAMPLE 3

Preparation of 8-Bromo-5,7,3',4'-Tetra-O-benzylepicatechin

Method A: To a solution of 116 mg (178 mol) of tetra-O-benzylepicatechin in 4 mL of anhydrous CH$_2$Cl$_2$ was added, with ice cooling and stirring, 32 mg (180 mol) of N-bromosuccinimide (NBS). Stirring at 0° C. was continued for 100 min, the solution was concentrated, and the residue was purified by chromatography on silica gel (15×1.8 cm) with chloroform/ethyl acetate (CHCl$_3$/EtOAc) (25:1). Crystallization from CHCl$_3$/ethanol gave 110 mg (85%) of a colorless, cotton-like solid. Mp 137.5° C.; $\alpha_D$–50.4°, $\alpha_{546}$– 60.7° (c 17.3 g/L, EtOAc); $^1$H NMR (300 MHz, CDCl$_3$, TMS) $\delta$ 7.5–7.25 (m, 20 H), 7.23 (d, 1 H, J=1.5 Hz), 7.03, 6.98 (ABq, 2 H, J=8.5 Hz, A part d with J=1 Hz), 6.25 (s, 1 H), 5.22 (s, 2 H), 5.19 (s 2 H), 5.11 (s, 2 H), 5.02, 4.96 (ABq, 2 H, J=9 Hz), 4.98 (s, 1 H) H, J=9 Hz), 4.27 (br s, 1 H), 3.04, 2.90 (ABq, 2 H, J=17.5 Hz, both parts d with J=1.5 and 4 Hz, resp.), 1.58 (d, 1 H, J=4.5 Hz); $^{13}$C NMR (75 MHz, CDCl$_3$, $\delta$ 156.86, 154.79, 151.65, 149.09, 148.73, 137.31, 137.15, 136.77, 136.72, 130.82, 128.67, 128.65, 128.58, 128.56, 128.09, 127.98, 127.87, 127.50, 127.31, 127.25, 127.13, 118.91, 115.17, 113.07, 102.85, 93.07, 78.62, 71.35, 71.20, 70.31, 65.92, 28.00; IR (mineral oil suspension) 3571, 1606, 1581, 1518, 1184, 1129, 771, 732, 694 cm$^{-1}$; MS m/z 399/397 (1/1%), 332(1%), 181 (8%), 91 (100%). Anal. calcd. for $C_{43}H_{37}O_6Br$: C, 70.78; H, 5.11. Found C, 70.47; H, 5.10.

Method B: To 563 mg (771 μmol) of 5,7,3',4-Tetra-O-benzyl-8-bromocatechin, prepared by the method described in Example 1, in 5 mL of $CH_2CL_2$ was added at room temperature all at once to 425 mg (1.00 mmol) of Dess-Martin periodinane. Water-saturated $CH_2Cl_2$ was added dropwise within 40 min to produce a slight turbidity. After another 20 min, 20 mL each of saturated $NaHCO_3$ solution and a 10% aqueous solution of $Na_2S_2O_3 \cdot 5H_2O$ were added. The phases were separated and the aqueous phase was extracted with 3×15 mL of ether. The combined organic phases were concentrated and the residue was filtered over silica gel (20×2.5 cm, ether/hexane 1:1). The eluate was evaporated and dried in vacuo to obtain 522 mg (93%) of the ketone as a colorless foam: $^1$H NMR ($CDCl_3$ 7.47–7.25 (m, 20 H), 7.04 (d, 1 H, J=1 Hz), 6.85, 6.81 (ABq, 2 H, J=8.5 Hz, B part d with=8.5 Hz), 3.52, 3.48 (ABq, 2 H, J-21.5 Hz); $^{13}$C NMR ($CDCl_3$ 203.99, 155.55, 155.40, 150.68, 148.98, 137.06, 136.90, 136.28, 136.04, 128.64, 128.62, 128.46, 128.41, 128.22, 128.05, 127.78, 127.76, 127.35, 127.17, 127.13, 127.08, 126.99, 118.86, 114.59, 112.43, 103.54, 93.96, 93.87, 82.91, 71.25, 71.04, 70.98, 70.38, 33.30; IR (film) 1734, 1605, 1513, 1099, 737 696 cm$^{-1}$.

To 598 mg (822 μmol) of the above crude ketone in 8.2 mL of anhydrous THF was added dropwise within 10 minutes 1.23 mL of a 1 M solution of lithium tri-sec-butylborohydride (L-Selectride®). After stirring at –78° C. for 3 hours, the starting material was still detectable in the reaction mixture by thin layer chromatography ("TLC"), ($SiO_2$, EtOAc/hexane 1:3), and another 1.23 mL of the reducing agent was added. Stirring was continued for another 4 hours while the temperature was gradually allowed to rise to –4° C. Aqueous sodium hydroxide (NaOH) (2.5 M, 6 mL) and 4 mL of 35% aqueous hydrogen peroxide ($H_2O_2$) were added with continued cooling; the resulting exotherm raised the bath temperature to +12° C. Stirring in the water bath was continued overnight, then the mixture was partially evaporated, and 20 mL ether and 10 mL of ethyl acetate (EtOAc) were added. The phases were separated, and the aqueous phase was extracted with 50 mL of EtOAc. The combined organic phases were evaporated, and the residue was purified by chromatography on silica gel (23×2.5 cm) with EtOAc/hexane 1:3 to obtain 327 mg (55%) of the product as a light-yellow foam.

EXAMPLE 4

5,7,3',4'-Tetra-O-benzyl-8-bromo-3-O-(tetrahydropyran-2-yl)catechin

To a solution of 297 mg (407 μmol) of 5,7,3',4'-Tetra-O-benzyl-8-bromoepicatechin in 2 mL of anhydrous methylene chloride ($CH_2Cl_2$) was added at room temperature 56 μL (0.61 μmol) of dihydropyran followed by 2.6 μL (40 μmol) of methanesulfonic acid. The gradually darkening solution was stirred at room temperature for 25 minutes after which period 0.15 mL of saturated aqueous sodium carbonate ($Na_2CO_3$) solution was added. After evaporation, the residue was chromatographed on silica gel ($SiO_2$) with ethyl acetate/hexane. A forerun was eluted with a mixing ratio of 1:4, the product (215 mg, 65%) with a ratio of 1:3, and unreacted starting material (97 mg, 33%) with a ratio of 1:2. Product: $^1$H NMR ($CDCl_3$) 7.50–7.25 (m, 20 H), 7.10 (s) and 7.08 (d, J=1 Hz) (1 H, two epimers), 6.94, 6.91 (ABq, 2 H, J=8.5 Hz), 6.22 (s, 1 H), 5.20–4.97 (m, 8 H), 4.88 (s) and 4.86 (s) (1 H, two epimers), 4.13–3.80 (m, 3 H), 3.42–2.87 (m, 3 H), 2.78 (dd, J=16.5, 8.5 Hz) and 2.61 (dd, J=16.5, 7 Hz) (1 H, two epimers), 1.77–1.18 (m, 5 H); IR (film) 1605, 1121, 1031, 735, 696 cm$^{-1}$.

EXAMPLE 5

5,7,3',4',5",7",3"',4"'- Octa-O-benzyl-8,8"-bicatechin

To a solution of 527 mg (648 mol) of the tetrahydropyranyl ether of Example 4 in 6.5 mL of anhydrous THF added dropwise at –78° C. within 5 min 0.91 mL (1.55 mmol) of tert-butyllithium (1.7 M in pentane). The resulting solution was stirred at –78° C. for 5 minutes while 1.5 mL of anhydrous tetrahydrofuran (THF) was added to 147 mg (0.91 mmol) of anhydrous ferric chloride ($FeCl_3$) (vigorous, exothermic reaction). The resulting solution/suspension was added within 2 minutes to the organolithium reagent, resulting in a black-brown solution. The reaction mixture was kept for 5 minutes at –78° C., then thawed to 0° C. within 1 hour. After addition of 1 mL of 5% HCl and partial evaporation, the product was extracted into 15 mL of chloroform ($CHCl_3$), and the organic phase was washed with 2×5 mL of 5% hydrochloric acid (HCl) and dried over magnesium sulfate ($MgSO_4$). The solvent was evaporated and replaced with 4 mL of THF to which 0.4 mL of 5% HCl was added. After 65 minutes at room temperature the reaction mixture was evaporated and the residue chromatographed on silica gel ($SiO_2$) with ethyl acetate/hexane mixtures. Initial elution with a ratio of 2:5 led to the recovery of 64 mg (15%) of 5,7,3',4'-Tetra-O-benzylcatechin. Further elution with a ratio of 1:2 gave two unidentified by-products, and finally 94 mg (22%) of the desired dimer was eluted with a ratio of 2:3. A 92 mg sample was further purified by preparative HPLC (Waters μPorasil 125 Å, 10 μm particle size, 30×5 cm, EtOAc/hexane 2:3, 80 mL/min, UV detection at 280 nm) to furnish 65 mg (16%) of the pure product as a colorless film: αD-75.2°, $α_{546}$-91.4° (EtOAc, c 18.3 gL$^{-1}$); $^1$H NMR ($CDCl_3$) δ 7.42–7.20 (m, 40 H), 6.90 (d, 2 H, J=1 Hz), 6.75, 6.67 (ABq, 4 H, J=8 H), 6.28 (s, 2 H), 5.03 (s, 4 H), 5.00–4.85 (m, 12 H), 4.59 (d, 2 H, J=8.5 Hz), 3.84 (m, 2 H), 2.95, 2.66 (ABq, 4 H, J=16.5 Hz, both parts d with J=5.5 and 8 Hz, resp.), 1.67 (br, 2 H); $^{13}$C NMR ($CDCl_3$) δ 156.64, 156.45, 153.02, 148.78, 148.68, 137.85, 137.22, 137.05, 131.80, 128.38, 128.31, 128.22, 127.71, 127.67, 127.58, 127.26, 127.17, 127.09, 126.58, 119.88, 114.44, 113.19, 105.46, 102.61, 92.51, 80.64, 71.14, 71.10, 69.78, 68.11, 27.20; IR (film) 3563, 3440 (br), 1602, 1264, 1120, 736, 697 cm$^{-1}$; MS (Electrospray, 0.1% HCOOH in $CH_3CN$) m/z 1323.1/1322.0 (M+Na)$^+$; calcd. for $^{13}C^{12}C_{85\ H74}O_{12}Na/^{12}C_{86}H_{74}O_{12}Na$:1322.5/1321.5), 968.8/967.8 (M+H)$^+$, then retro-Diels-Alder reaction; calcd. for $^{13}C^{12}C_{63}H_{55}O_9/^{12}C_{64}H_{55}O_9$: 968.4/967.4).

EXAMPLE 6

5,7,3'4',5",7",3"',4"'- Octa-O-benzyl-3,3" -di-O- (tri-O-benzylgalloyl) - 8,8"- bicatechin To a solution of 63.5 mg (144 mol, 5 eq.) of tri-O-benzylgallic acid and 1.5 μL of dimethylformamide (DMF) in 1 mL of methylene chloride ($CH_2Cl_2$) was added 25 μL (0.29 μmol, 10 eq.) of oxalyl chloride. After stirring at room temperature under a calcium chloride ($CaCl_2$) tube for 35 min, the mixture was evaporated and dried in vacuo. To the crude acid chloride was added a solution of 37.5 mg (28.9

µmol) of the 8,8"-dimer of Example 5 in 0.8 mL of anhydrous pyridine and 17.6 mg (144 µmol, 5 eq.) of 4-di (methylamino)pyridine (DMAP). The mixture was stirred at room temperature in a closed vial for 24.5 hours. After addition of 50 µL of water, stirring at room temperature was continued for 4 hours. Then 15 mL of 5% hydrochloric acid (HCl) was added, and the product was extracted into 3×5 mL of methylene chloride ($CH_2Cl_2$). The organic phases were dried over magnesium sulfate ($MgSO_4$) and evaporated, and the crude material was purified by filtration over silica gel ($SiO_2$) (15×1.8 cm) with ethyl acetate (EtOAc)/$CHCl_3$/ hexane 1:9:10. Evaporation and drying in vacuo gave 58.2 mg of a colorless film which was further purified by preparative TLC ($SiO_2$, 200×200×2 mm, EtOAc/hexane 1:2) to yield 55.0 mg (89%) of the product: $\delta_D$-31.4, $\delta_{546}$-36.9 (EtOAc, c 15.4 g$L^{-1}$); $^1$H NMR ($CDCl_3$) δ7.40–7.15 (m, 70 H), 6.85 (s, 2 H), 6.68, 6.36 (ABq, 4 H, J=8.5 Hz), 6.34 (s, 2 H), 5.25 (m, 2 H), 5.05 (s, 4 H), 5.03–4.92 (m, 10 H), 4.84 (s, 8 H), 4.83 (s, 4 H), 4.77, 4.71 (ABq, 4 H, J=11.5 Hz), 2.87, 2.78 (ABq, 4 H, J=16.5 Hz, both parts d with J=5.5 and 4.5 Hz, resp.); $^{13}$C NMR ($CDCl_3$) δ164.84, 156.63, 156.46, 153.16, 152.24, 148.65, 148.41, 142.52, 137.82, 137.64, 137.30, 137.06, 137.02, 136.69, 131.90, 128.46, 128.39, 128.31, 128.20, 128.11, 127.80, 127.74, 127.60, 127.53, 127.31, 127.13, 127.06, 126.47, 124.99, 119.19, 114.34, 112.39, 109.08, 105.40, 102.00, 91.93, 75.06, 70.98, 70.89, 70.02, 69.94, 23.02; IR (film) 1714, 1596, 1428, 1125, 735, 696 $cm^{-1}$. Anal. Calcd. for $C_{142}H_{118}O_{20}$: C, 79.42; H, 5.81. Found: C, 79.53; H, 5.55.

EXAMPLE 7

3,3"-Di-O-galloyl-8,8"-bicatechin

A solution of 29.2 mg (13.6 µmol) of the preceding compound in 2 mL of THF and 2 mL of MeOH was hydrogenated at atmospheric pressure (balloon) over 34.5 mg of commercial (wet) 20% Pd(OH)$_2$/C for 105 min. The catalyst was filtered off over cotton and washed with 2 mL of MeOH. After evaporation, the crude product was purified by preparative HPLC (Waters Bondapak $C_{18}$, 300×19 mm, flow rate 9 mL/min, UV detection at 280 nm) using the following gradient of solvent B (0.5% AcOH in denatured EtOH) in solvent A (0.5% AcOH in $H_2O$): 0–1 min, 15% B; 1 to 15 min, 15 to 26% B; 15 to 16 min, 26 to 80% B; 16 to 20 min, 80% B. The combined eluates containing the major component were evaporated and dried in vacuo to give 6.7 mg (56%) of the product as a purplish film: $^1$H NMR (acetone-$d_6$/$D_2O$ 3:1 v/v) 7.06 (s, 4 H), 7.03 (d, 2 H, J=2 Hz), 6.86, 6.76 (ABq, 4 H, J=8 Hz, A part d with J=1.5 Hz), 6.19 (s, 2 H), 5.23 (m, 2 H), 4.99 (d, 2 H, J=8 Hz), 3.05, 2.64 (ABq, 4 H, J=16 Hz, both parts d with J=5.5 and 8 Hz, resp.); $^{13}$C NMR (acetone-$d_6$/$D_2O$ 3:1 v/v) 166.59, 155.92, 155.59, 154.26, 145.81, 145.27, 145.19, 139.00, 131.30, 121.08, 119.58, 115.74, 114.76, 109.95, 100.89, 99.41, 96.08, 78.89, 71.36, 25.97; MS (Electrospray, McOH/ $CH_3CN$) m/z 906.4/905.4 (M+Na$^+$; calcd. for $^{13}C^{12}C_{43}$ $H_{34}O_{20}$Na/$^{12}C_{44}H_{34}O_{20}$Na: 906.2/905.2), 735.6 (M+Na$^+$- gallic acid; calcd. for $^{12}C_{37}H_{28}O_{15}$Na: 735.1), 601.7 (M+Na)$^+$, then retro-Diels-Alder reaction; calcd for $^{12}C_{29}H_{22}O_{13}$Na: 601.1).

EXAMPLE 8

Preparation of 5,7,3',4'-Tetra-O-benzylcatechin

A solution of (+)-catechin (65.8 g, 226.7 mmol, anhydrous), dissolved in anhydrous dimethylformamide (DMF, 720 mL), was added dropwise, at room temperature over a period of 80 minutes, to a stirred suspension of sodium hydride, (60% in oil, 39 g, 975 mmol, 4.3 eq.) in dimethylformamide (DMF) (180 mL). (S. Miura, et al., *Radioisotopes*, 32, 225–230 (1983)). After stirring for 50 minutes, the flask was placed in a −10° C. NaCl/ice bath. Benzyl bromide (121 mL, 1.02 mol, 4.5 eq.) was added dropwise within 80 min. and the brown reaction mixture was warmed to room temperature, with stirring, overnight. The resulting reaction mixture was evaporated and the resulting candy-like solid was dissolved, with heating and stirring, in two portions of solvent each consisting of 200 mL of chloroform ($CHCl_3$) and 100 mL of water. The phases were separated, the aqueous phase was extracted with $CHCl_3$ (20 mL), and the combined organic phases were washed with water (100 mL), dried over magnesium sulfate ($MgSO_4$) and evaporated. The residue was purified by chromatography on silica gel (42×10 cm; ethyl acetate/chloroform/hexane 1:12:7) to provide, after evaporation and drying in vacuo, 85 g of the crude product, which was recrystallized from trichloroethylene (1.3 L) to provide 35.1 g (24%) of an off-white powder. $^1$H NMR ($CDCl_3$) 7.47–7.25 (m, 20 H), 7.03 (s, 1 H), 6.95 (s, 2 H), 6.27, 6.21 (ABq, 2 H, J=2 Hz), 5.18 (s, 2 H), 5.17 (narrow ABq, 2 H), 5.03 (s 2 H), 4.99 (s 2 H), 4.63 (d, 1 H, J=8.5 Hz), 4.00 (m, 1 H), 3.11, 2.65 (ABq, 2 H, J=16.5 Hz, both parts d with J=5.5 and 9 Hz, resp.), 1.59 (d, 1 H, J=3.5 Hz); IR (film) 3440 (br), 1618, 1593, 1513, 1499, 1144, 1116, 733, 696 $cm^1$; MS m/z 650 (M$^{+\cdot}$ 0.5%), 319, 181, 91.

Alternatively, the tetra-O-benzyl (+) - catechin may be prepared using the method described by H. Kawamoto et al, *Mokuzai Gakkaishi*, 37, (5) 488–493 (1991), using potassium carbonate and benzyl bromide in dimethyl formamide (DMF). Partial racemization of catechin, at both the 2- and 3-positions, was observed by M.-C. Pierre et al., *Tetrahedron Letters*, 38 (32) 5639–5642 (1997).

EXAMPLE 9

Preparation of 5,7,3',4'-Tetra-O-benzylepicatechin

A 1 M solution of lithium tri-sec-butylborohydride in tetrahydrofuran, (THF) (100 mL, L-Selectride®, sold by the Aldrich Chemical Co, Inc., Milwaukee, Wis.) was added, under an argon atomsphere, to a stirred, 0° C. solution of anhydrous lithium bromide, (LiBr) (34.9 g, 402 mmol) in 100 mL of anhydrous THF. The resulting mixture was cooled to −78° C., using an acetone/$CO_2$ bath, followed by dropwise addition of a solution of the protected epicatechin (50.1 g, 77.2 mmol) in 400 mL of anhydrous THF, over a period of 50 min. Stirring was continued at −78° C. for 135 minutes. The cooling bath was removed and 360 mL of 2.5 M aqueous sodium hydroxide (NaOH) was added to the reaction mixture. The reaction flask was placed in a room temperature water bath and a mixture of 35% aqueous hydrogen peroxide $H_2O_2$ (90 mL) and ethanol (270 mL) was added over a period of 130 min. Stirring was continued overnight. Chloroform (700 mL) was added to dissolve the crystallized product, the phases were separated, the aqueous phase was extracted with chloroform ($CHCl_3$) (50 mL), the combined organic phases were dried over magnesium sulfate ($MgSO_4$), evaporated and dried in vacuo to provide 56.6 g of the crude product. This material was dissolved in 600 mL of a boiling mixture of ethyl acetate (EtOAc) and ethanol (EtOH) (2:3) and allowed to crystallize at room temperature and then in the refrigerator. The product was isolated by suction filtration, washed with 2×50 mL of cold (−20° C.) EtOAc/EtOH (1:3), and dried in vacuo first at room temperature, then at 80° C. to obtain 35.4 g (70%) of a light yellow solid. The evaporated mother liquor was filtered over silica gel ($SiO_2$), (14×6.5 cm, chloroform ($CHCl_3$), and then $CHCl_3$/EtOAc 12:1), the eluate was concentrated to 40 mL, and the residue was diluted with 60 mL of ethanol, to obtain an additional 5.5 g (11%) of the O-benzylepicatechin as a yellow solid: mp 129.5–130° C. (from EtOAc/EtOH); $\alpha_D$-27.7°, $_{546}$-33.4° (EtOAc, c 21.6 g/L); $^1$H NMR ($CDCl_3$) 7.48–7.25 (m, 20 H), 7.14 (s, 1 H), 7.00, 6.97 (ABq, 2 H, J=8.5 Hz, A part d with J=1.5 Hz), 6.27 (s, 2 H), 5.19 (s, 2 H), 5.18 (s, 2 H), 5.02 (s, 2 H), 5.01 (s2 H, 4.91 (s 1 H), 4.21 (br s, 1 H), 3.00 2.92 (ABq, 2 H, J=17.5 Hz, both parts d with J=1.5 and 4 Hz, resp.), 1.66 (d, 1 H, J=5.5 Hz); Anal. Calcd. for $C_{43}H_{48}O_6$: C, 79.36; H, 5.89. Found: C, 79.12: H, 5.99.

EXAMPLE 10

5,7,3',4'-Tetra-O-benzyl-6,8-dibromoepicatechin

To a solution of 334 mg (914 mol) of 5,7,3',4'-Tetra-O-benzylepicatechin in 10 mL of anhydrous $CH_2Cl_2$ was added with ice cooling all at once 192 mg (1.08 mmol) of recrystallized N-bromosuccinimide (NBS). The reaction mixture was stirred at 0° C. for 45 min and at room temperature for 17 h. A solution of 200 mg of $Na_2S_2O_3 5H_2O$ in 5 mL of water was added. After brief stirring, the phases were separated, the aqueous phase was extracted with 5 mL of $CH_2Cl_2$, and the combined organic phases were dried over $MgSO_4$ and evaporated. Chromatography on silica gel (30× 2.6 cm) with EtOAc/$CHCl_3$/hexane 1:12:7 (to remove a trace of byproduct) then 3:12:7, was followed by evaporation and drying in vacuo to give 362 mg (87%) of the dibromide as a colorless foam: $[]_{546}$-58.2° (EtOAc, c 13.5 gL$^{-1}$; $^1$H NMR ($CDCl_3$) δ 7.64 (d, 2 H, J=7 Hz), 7.52–7.26 (m, 18 H), 7.17 (s, 1 H), 7.03, 6.97 (s, 2 H), 5.20 (s, 2 H), 5.17 (s, 2 H), 5.03 (s, 2 H), 5.01, 4.97 (ABq, 2 H, J=11 Hz), 4.99 (s, 1 H), 4.19 (narrow m, 1 H), 3.04, 2.87 (ABq, J=17.5 Hz, both parts d with J=1.5 and 3.5 Hz, resp.), 1.55 (d, 1 H, J=3.5 Hz); $^{13}$C NMR ($CDCl_3$) δ 154.43, 152.57, 151.09, 149.03, 148.82, 137.10, 136.94, 136.50, 136.37, 130.13, 128.52, 128.50, 128.48, 128.47, 128.43, 128.35, 128.32, 128.16, 127.82, 127.81, 127.36, 127.20, 118.81, 115.06, 112.91, 112.30, 105.23, 103.25, 78.80, 74.61, 74.55, 71.24, 71.14, 65.33, 28.75; IR (film) 1734, 1606, 1513, 1369, 1266, 1184, 1113, 1083, 735, 697 cm$^{-1}$. Anal. Calcd. for $C_{43}H_{36}O_6Br_2$: C, 63.88; H, 4.49. Found C, 64.17; H, 4.45.

EXAMPLE 11

5,7,3',4'-Tetra-O-benzyl-6-bromo-3-O-(tetrahydropyran-2-yl)catechin

To a solution of 297 mg (407 μmol) of 5,7,3',4'-Tetra-O-benzyl-6-bromoepicatechin in 2 mL of anhydrous $CH_2Cl_2$ is added at room temperature 56 μL (0.61 mmol) of dihydropyran followed by 2.6 μL (40 μmol) of methanesulfonic acid. The solution is stirred at room temperature for 25 min after which period 0.15 mL of saturated aqueous $Na_2CO_3$ solution is added. After evaporation, the residue is chromatographed on $SiO_2$ with EtOAc/hexane.

EXAMPLE 12

5,7,3',4',5'',7'',3''',4'''- Octa-O-benzy-6,6' bicatechin

To a solution of 527 mg (648 μmol) of the (tetrahydropyranyl ether) compound of Example 9 in 6.5 mL of anhydrous THF is added dropwise at −78° C. within 5 min 0.91 mL (1.55 mmol) of tert-butyllithium (1.7 M in pentane). The resulting solution is stirred at −78° C. for 5 min while 1.5 mL of anhydrous THF is added to 147 mg (0.91 mmol) of anhydrous $FeCl_3$ (vigorous, exothermic reaction). The resulting solution/suspension is added within 2 min to the organolithium reagent. The reaction mixture is kept for 5 min at −78° C., then thawed to 0° C. within 1 hour. After addition of 1 mL of 5% HCl and partial evaporation, the product is extracted into 15 mL of $CHCl_3$, and the organic phase is washed with 2×5 mL of 5% HCl and dried over $MgSO_4$. The solvent is evaporated and replaced with 4 mL of THF to which 0.4 mL of 5% HCl is added and the residue is purified.

EXAMPLE 13

5,7,3',4',5'',7'',3''',4'''- Octa-O-benzyl-3,3'' -di-O-(tri-O-benzylgalloyl)-6,6''-bicatechin To a solution of 63.5 mg (144 μmol, 5 eq.) of tri-O-benzylgallic acid and 1.5 μL of DMF in 1 mL of $CH_2Cl_2$ is added 25 μL (0.29 mmol, 10 eq.) of oxalyl chloride. After stirring at room temperature under a $CaCl_2$ tube for 35 min, the mixture is evaporated and dried in vacuo. To the crude acid chloride is added a solution of 37.5 mg (28.9 μmol) of the 5,7,3',4'-tetra-O-benzyl-6,8-dibromoepicatechin of Example 10, in 0.8 mL of anhydrous pyridine and 17.6 mg (144 μmol, 5 eq.) of DMAP. The mixture is stirred at room temperature in a closed vial for 24.5 hours. After addition of 50 μL of water, stirring at room temperature is continued for 4 hours. Then 15 mL of 5% HCl is added, and the product is extracted into 3×5 mL of $CH_2Cl_2$. The organic phases are dried over $MgSO_4$ and evaporated, and the crude material is purified by filtration over $SiO_2$ (15×1.8 cm) with EtOAc/$CHCl_3$/hexane 1:9:10. Evaporation and drying in vacuo provides a film which is further purified by chromatography to yield the product.

EXAMPLE 14

3,3''- Di-O-galloyl-6,6''-bicatechin

A solution of 29.2 mg (13.6 μmol) of the compound of Example 8 in 2 mL of THF and 2 mL of MeOH is hydrogenated at atmospheric pressure (balloon) over 34.5 mg of commercial (wet) 20% Pd(OH)$_2$/C for 105 min. The catalyst is filtered off over cotton and washed with 2 mL of MeOH. After evaporation, the crude product is purified by preparative HPLC.

What claimed is:

1. A (8↔8) catechin and/or epicatechin dimer.
2. A (6↔6) catechin and/or epicatechin dimer.
3. A (6↔8) catechin and/or epicatechin dimer.
4. A (8↔8) catechin and/or epicatechin dimer digallate.
5. A (6↔6) catechin and/or epicatechin dimer digallate.
6. A (6↔8) catechin and/or epicatechin dimer digallate.
7. A process for preparing the (8↔8) catechin and/or epicatechin dimer of claim 1, which comprises the steps of:
   a. protecting the phenolic hydroxyl groups of an epicatechin and/or catechin monomer with a first protecting group;
   b. protecting the C-3 hydroxyl groups of the compounds of step (a) with a second protecting group;
   c. halogenating the C-8 positions of the the compounds of step (b);
   d. reacting the compounds of step (c) with an alkyllithium compound to introduce lithium at the C-8 positions;
   e. oxidatively or reductively coupling the compounds of step (d) to form a protected dimer; and f. deprotecting the compound of step (e) to form the (8↔8) dimer.

8. A process for preparing the (6↔6) catechin and/or epicatechin dimer of claim 2, which comprises the steps of:
   a. protecting the phenolic hydroxyl groups of a catechin and/or epicatechin monomer with a first protecting group;
   b. halogenating the compounds of step (a) to introduce halo groups at the C-6 and at the C-8 positions;
   c. protecting the C-3 hydroxyl groups of the compounds of step (b) with a second protecting group;
   d. selectively removing from the compounds of step (c) the halo groups at the C-8 positions;
   e. reacting the compounds of step (d) with an alkyllithium compound to introduce lithium at the C-6 positions;
   f. oxidatively or reductively coupling the compounds of step (e) to form a protected dimer; and
   g. deprotecting the compound of step (f) to form the (6↔6) dimer.

9. A process for preparing the (6↔8) catechin and/or epicatechin dimer of claim 3, which comprises the steps of:
   a. halogenating a first catechin or epicatechin monomer to form the 8-halo compound;
   b. halogenating a second catechin or epicatechin monomer to form the 6-halo compounds;
   c. oxidatively or reductively coupling the compounds of step (a) and step (b); and
   d. separating the (8↔8), (6↔6), and (6↔8) dimers.

10. A process for preparing the (8↔8) catechin and/or epicatechin dimer digallate of claim 4, which comprises the steps of:
    a. protecting the C-3 hydroxyl groups of a catechin and/or epicatechin monomer with a first protecting group;
    b. protecting the phenolic hydroxyl groups of the compounds of step (a) with a second protecting group;
    c. halogenating the compounds of step (b) to introduce a halo group at the C-8 positions;
    d. reacting the compounds of step (c) with an alkyl lithium compound to introduce lithium at the C-8 position;
    e. oxidatively or reductively coupling the compounds of step (d);
    f. deprotecting the 3-hydroxyl positions of the compound of step (e);
    g. esterifying the compound of step (f) with a tri-O-benzylgalloyl halide to form the protected dimer digallate; and
    h. deprotecting the compound of step (g) to form the (8↔8) dimer digallate.

11. A process for preparing the (6↔6) catechin and/or epicatechin dimer digallate of claim 5, which comprises the steps of:
    a. protecting the C-3 hydroxyl groups of a catechin and/or epicatechin monomer with a first protecting group;
    b. protecting the phenolic hydroxyl groups of the compounds of step (a) with a second protecting group;
    c. halogenating the compounds of step (b) to introduce a halo group at the C-6 positions;
    d. reacting the compounds of step (c) with an alkyl lithium compound to introduce lithium at the C-6 position;
    e. oxidatively or reductively coupling the compounds of step (d).
    f. deprotecting the 3-hydroxyl positions of the compounds of step (e);
    g. esterifying the compound of step (f) with a tri-O-benzylgalloyl halide to form the protected dimer digallate; and
    h. deprotecting the compound of step (g) to form the (6↔6) dimer digallate.

12. A process for preparing the (6↔8) catechin and/or epicatechin dimer digallate of claim 6, which comprises the steps of:
    (a) halogenating a first catechin or epicatechin monomer to form a 8-halo compound;
    (b) halogenating a second catechin or epicatechin monomer to form a 6-halo compounds;
    (c) oxidatively or reductively coupling the compounds of step (a) and step (b);
    (d) separating the (8↔8), (6↔6), and (6↔8) dimers;
    (e) protecting the phenolic hydroxyl groups of the separated (6↔8) dimer of step (d);
    (f) esterifying the compound of step (e) with tri-O-benzylgalloyl halide to form the protected dimer digallate; and
    (g) deprotecting the compound of (f) to form the (6↔8) dimer digallate.

13. The process of claims 7, 8, 9, 10, 11, or 12 wherein the coupling is an oxidative coupling.

14. The process of claim 9, wherein the first and second protecting groups are benzyl or benzyl and tetrahydropyranyl or tert-butyldimethysilyl.

15. The process of claims 7, 8, or 11, wherein the halogenating agent is N-bromosuccinimide; wherein the alkyllithium is tert-butyllithium or N-butyllithium; and wherein the deprotecting step is carried out by catalytic hydrogenolysis.

16. The process of claim 13, wherein the oxidative coupling is effected by ferric chloride.

17. The process of claims 10, 11, or 12, wherein the tri-O-benzylgalloyl halide is a tri-O-benzylgalloyl chloride.

* * * * *